(12) United States Patent
Painchaud et al.

(10) Patent No.: US 11,612,729 B2
(45) Date of Patent: Mar. 28, 2023

(54) IMPLANT INJECTION DEVICE PROVIDED WITH SEQUENTIALLY RELEASED PUSHING MEANS

(71) Applicant: Nemera La Verpillière, La Verpilliere (FR)

(72) Inventors: Gaëtan Painchaud, Francheville (FR); Pascal Dugand, Estrablin (FR); Thomas Megard, La Roche-Vineuse (FR)

(73) Assignee: Nemera La Verpillière

( * ) Notice: Subject to any disclaimer, the term of this patent is extended or adjusted under 35 U.S.C. 154(b) by 790 days.

(21) Appl. No.: 16/388,275

(22) Filed: Apr. 18, 2019

(65) Prior Publication Data
US 2019/0351208 A1 Nov. 21, 2019

(30) Foreign Application Priority Data
Apr. 18, 2018 (FR) ........................................ 1853405

(51) Int. Cl.
*A61M 37/00* (2006.01)
*A61M 5/32* (2006.01)
(Continued)

(52) U.S. Cl.
CPC ........ *A61M 37/0069* (2013.01); *A61M 5/322* (2013.01); *A61M 5/5013* (2013.01); *A61B 17/3468* (2013.01)

(58) Field of Classification Search
CPC .............. A61M 37/0069; A61M 5/322; A61M 5/321; A61M 5/3205; A61M 5/32;
(Continued)

(56) References Cited

U.S. PATENT DOCUMENTS

| 4,403,610 | A | * | 9/1983 | Lodge | A61M 37/0069 604/61 |
| 4,994,028 | A | | 2/1991 | Leonard et al. | |
| 5,281,197 | A | * | 1/1994 | Arias | A61M 37/0069 604/209 |
| 5,284,479 | A | * | 2/1994 | de Jong | A61M 37/0069 604/130 |
| 5,540,662 | A | * | 7/1996 | Nicholson | A61M 25/0637 604/164.11 |

(Continued)

FOREIGN PATENT DOCUMENTS

| WO | 2004026106 A2 | 4/2004 |
| WO | 2006071554 A2 | 7/2006 |

*Primary Examiner* — Emily L Schmidt
*Assistant Examiner* — Alexandra Lalonde
(74) *Attorney, Agent, or Firm* — St. Onge Steward Johnston & Reens LLC

(57) ABSTRACT

An implant injection device includes an injection needle, a receiver housing receiving at least a first implant and a second implant, an injection mechanism, including a pushing rod arranged upstream from the implants and configured to push the implants through the injection needle between an initial position and a final position in which the implants are injected, a pushing device for pushing on the pushing rod, configured to exert a force to move the pushing rod from the initial position to the final position, an intermediate stop device holding the pushing rod in an intermediate position and opposing the force exerted by the pushing device when a stroke of the pushing rod reaches a predetermined distance corresponding to a length of injection of the first implant, and an actuator for actuation by a user, configured to release the pushing rod from the intermediate position to the final position.

16 Claims, 2 Drawing Sheets

(51) Int. Cl.
*A61M 5/50* (2006.01)
*A61B 17/34* (2006.01)

(58) Field of Classification Search
CPC ...... A61M 5/31; A61M 5/178; A61M 5/5013;
A61M 5/50; A61M 31/007; A61M
5/3158; A61M 5/315; A61M 5/31501;
A61M 5/31505; A61M 5/3153; A61M
5/31593; A61M 5/31595; A61M
2005/31506; A61M 2005/31508; A61M
2005/3151; A61B 17/3468; A61B 17/34;
A61D 7/00; A61F 9/0017
See application file for complete search history.

(56) References Cited

U.S. PATENT DOCUMENTS

| | | | | |
|---|---|---|---|---|
| 5,554,124 | A * | 9/1996 | Alvarado | A61B 17/3462 |
| | | | | 604/248 |
| 6,270,472 | B1 | 8/2001 | Antaki et al. | |
| 6,402,716 | B1 * | 6/2002 | Ryoo | A61M 37/0069 |
| | | | | 604/60 |
| 2004/0127765 | A1 | 7/2004 | Seiler et al. | |
| 2005/0165363 | A1 * | 7/2005 | Judson | A61M 5/31551 |
| | | | | 604/209 |
| 2009/0281520 | A1 | 11/2009 | Highley et al. | |
| 2015/0105719 | A1 * | 4/2015 | Haindl | A61B 17/3403 |
| | | | | 604/165.02 |
| 2015/0360019 | A1 * | 12/2015 | Clancy | A61M 37/0069 |
| | | | | 600/432 |
| 2016/0296739 | A1 | 10/2016 | Cleveland | |

\* cited by examiner

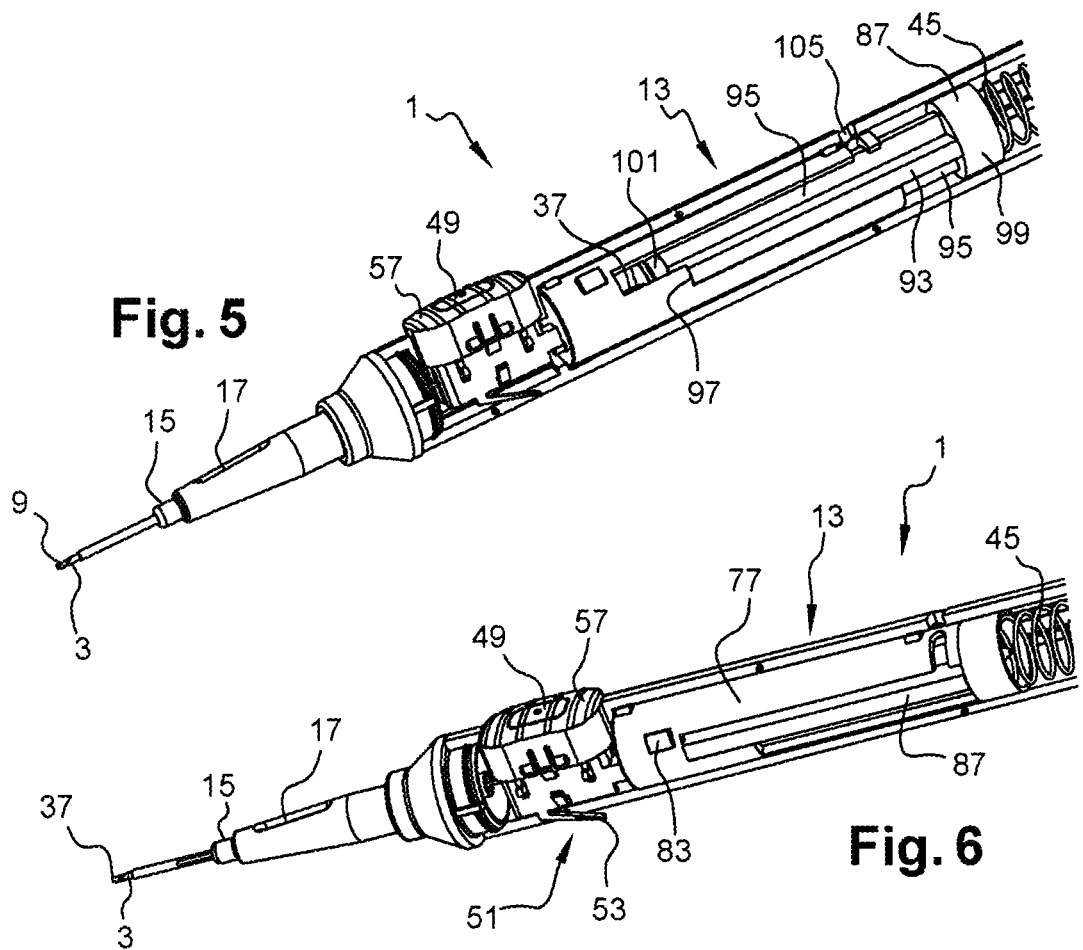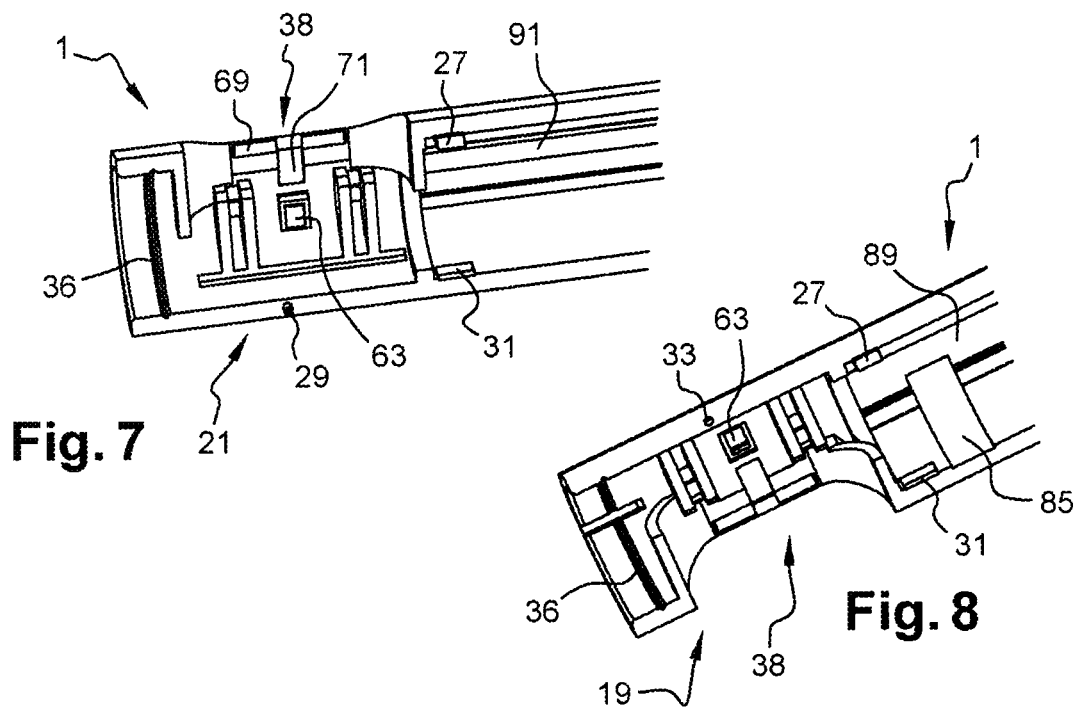

IMPLANT INJECTION DEVICE PROVIDED WITH SEQUENTIALLY RELEASED PUSHING MEANS

FIELD OF THE INVENTION

The invention relates to the technical field of injecting one or more implants into a patient's body.

BACKGROUND OF THE INVENTION

In particular, document US20090281520A1 describes an implant injection device in which the implant can be injected by slidably pressing a button, the button then being pressed by the user in a direction substantially parallel to the injection direction. Thus, before actuation, the pushing rod is retracted and the button is located on the side of the proximal end of the device, in other words the end opposite the injection end. When the user slidably presses the button, the button slides in a direction substantially parallel to the injection direction and moves the pushing rod, which pushes the implant and allows its injection.

However, with such actuation by slidably pressing, the user is unable to inject several implants easily. This actuation is generally carried out by the user's thumb, which has a limited actuation stroke. This limited stroke is insufficient for the successive injection of two implants. In addition, with such actuation, good injection accuracy cannot be maintained over a long stroke and in particular the injection cannot be stopped once the implant has been injected, for example to direct the injection needle in another direction for a second implant to avoid injecting too deeply. With such actuation, there is in fact a risk of accidentally starting to inject an implant after the implant already injected. This is not desirable to guarantee correct injection, in particular to avoid breaking at least one of the implants or injuring the patient.

Thus, in view of their actuation type, these implant injection devices cannot be used to easily inject a plurality of implants.

SUMMARY OF THE INVENTION

This invention aims in particular to provide an implant injection device which can be used to easily inject a plurality of implants while controlling the injection of each implant.

Thus, the invention relates in particular to an implant injection device comprising:
an injection needle,
a receiver housing for receiving at least a first implant and a second implant,
injection means, comprising:
  a pushing rod, arranged upstream from said implants housed in the receiver housing and configured to push the first implant and the second implant through the injection needle between an initial position and a final position in which the first implant and the second implant are injected,
  means for pushing on the pushing rod, configured to exert a force tending to move the pushing rod from the initial position to the final position,
  intermediate stop means holding the pushing rod in an intermediate position between the initial position and the final position, said means oppose the force exerted by the pushing means when the stroke of the pushing rod reaches a predetermined distance corresponding to the length of injection of the first implant,
  means for actuation by a user, configured to release a displacement of the pushing rod from the intermediate position to the final position.

Thus, it is proposed to perform the injection sequentially, considering the injection of each implant as a sequence starting with a displacement of the pushing rod, the pushing means then acting on the pushing rod to allow the injection of a first implant, and ending by the pushing means being stopped by the stop means to avoid injecting the next implant, called second implant. For each respective implant injection, the user actuates the actuation means which release a displacement of the pushing rod in order to inject the respective implant. When the stroke of the pushing rod corresponds to the respective injection length required for this respective implant, the pushing means are stopped by the stop means, without the need for the user to control or actuate any element. The user can therefore concentrate on positioning the injection needle and thus on positioning the respective implant in the patient's body. The user controls easily and as required the release of each implant via the actuation means.

We can see that it is particularly useful to be able to inject implants sequentially. In particular, this may allow the user activating the actuation button to resume its stroke and therefore avoid losing any precision when injecting the next implant. Or, this allows the direction of the needle to be changed in order to inject a second implant in a direction other than that of the first implant and thus avoid injecting too deeply, which could be the case during a continuous injection of the implants.

An "implant" is preferably understood to mean a pharmaceutical compound in solid or semi-solid state, for example in the form of an encapsulated liquid and/or an electronic component, for example an RFID type electronic chip. A "patient" or "subject" is generally understood to mean a living being, for example a mammal, in particular a human being. The user is generally a person different from the patient but the user may be the patient himself.

In this description, it is understood that the distal direction designates the direction farthest away from a user's fingers, in other words closest to the skin or the surface of a patient at the time of an injection, and the proximal direction designates the direction opposite to the distal direction. In other words, it is considered that the distal direction and the distal sense are the direction and sense which go towards the "front" of the implant injection device, a direction also called the injection direction. In particular, the distal end of a part corresponds to the end located on the side of the injection needle and the proximal end corresponds to the opposite end. It is also understood that the injection axis, which is the injection direction, corresponds to the axis of the implant injection device defined by the axis of the injection needle.

Consequently, it is understood that the "downstream" direction is a direction opposite to the "upstream" direction and corresponds to the direction towards the distal end of the implant injection device, in other words towards the injection site, towards the end configured to be in contact with the implant injection site. Thus, the "downstream" direction may also be called the injection direction. It is understood that the terms "upstream" and "downstream" designate the distal and proximal directions, a downstream element being arranged further away in the distal direction than an upstream element.

Advantageously, the stops means are configured so as to generate a sensory indication, such as a tactile or audible indication, when the pushing rod reaches its intermediate position held by the intermediate stop means.

The implant injection device may further comprise one or more of the following characteristics, taken alone or in combination.

The implant injection device comprises initial stop means opposing the force exerted by the pushing means and holding the pushing rod in the initial position.

Thus, using the initial stop means, the injection of a first implant cannot be triggered accidentally.

The actuation means comprise an actuation button which can be moved by pressing by a user between:
- a rest position before actuation,
- a median position, in which the actuation means release the displacement of the pushing rod from its initial position to its intermediate position, and
- a terminal position, in which the actuation means release the displacement of the pushing rod from its intermediate position to its final position.

Thus, actuation is carried out sequentially by the user, in a way which is particularly easy.

The actuation means comprise an indication element configured to indicate to a user that the actuation button is in its median position, the indication element preferably comprising a secondary button flush with the actuation button when the latter is in its median position.

Thus, using the indication element, the user can easily see or detect the current injection stage of the implant injection device. Obviously, other types of indication element can be considered. A tactile and/or audible indication element is particularly advantageous, this indication being very practical since the user does not have to look at the implant injection device and can concentrate on looking at the injection area.

The actuation means comprise means for returning the actuation button to its rest position, in particular an elastic tab carried by the actuation button, or a spring.

Thus, the user must supply a certain force to actuate the actuation button, which avoids accidentally triggering the injection of an implant, for example to direct the injection needle in another direction for a subsequent implant such as a second implant, to avoid injecting too deeply.

The implant injection device comprises non-return means preventing the actuation button from returning respectively from its median position and from its terminal position.

Thus, when the injection of a respective implant is complete, the actuation button can only be actuated for the injection of other implants arranged upstream, or can no longer be used if the respective implant was the last implant to be injected. Thus, the actuation button is actuated only over the stroke required to inject the next implant. In addition, the implant injection device is not reusable, thereby respecting hygiene constraints relating to this type of implant injection device.

The actuation means are lateral, for example movable by sliding in a radial direction relative to the longitudinal axis of the pushing rod or by pivoting about an axis orthogonal to the longitudinal axis of the pushing rod.

In other words, the user presses in a direction perpendicular to the injection direction, unlike an axial press, in particular on the proximal end of the implant injection device. Thus, actuation of the implant injection device is easy for a user, since the force does not have to be exerted parallel to the injection direction.

The intermediate stop means comprise an intermediate axial stop member holding the pushing rod in the intermediate position, the intermediate axial stop member being configured to be driven by the actuation means to release a displacement of the pushing rod from the intermediate position to the final position.

Thus, this increases the safety of the implant injection device. Using an intermediate axial stop member stops the stroke of the pushing rod and consequently the injection, once an implant has been injected.

The initial stop means comprise an initial axial stop member holding the pushing rod in the initial position, the initial axial stop member being configured to be driven by the actuation means to release a displacement of the pushing rod from the initial position to the intermediate position.

Thus, this increases the safety of the implant injection device. Using an initial axial stop member holds the pushing rod in its initial position and consequently prevents the injection of a first implant.

The actuation means cause the rotation of at least one from the initial axial stop member and the intermediate axial stop member to release respectively a displacement of the pushing rod from the initial position to the intermediate position and/or from the intermediate position to the final position.

Thus, it is proposed to use a cam type movement transmission, so that actuation by the user pressing is converted into a rotation releasing the displacement of the pushing rod, in order to limit the stroke to be supplied by the user, for example by one of the user's fingers.

The intermediate axial stop member and the initial axial stop member are made in one piece forming an axial stop member, and are formed by a partly hollowed out cylinder which is directed substantially longitudinally, whose side wall comprises a plurality of successive indents in the shape of steps.

Thus, the initial stop means and the intermediate stop means are particularly easy to make.

The implant injection device comprises final stop means opposing the force exerted by the pushing means and holding the pushing rod in the final position.

The final stop means comprise a final axial stop member holding the pushing rod in the final position.

The initial axial stop member, the intermediate axial stop member and the final axial stop member are made in one piece forming an axial stop member, and are formed by a partly hollowed out cylinder which is directed substantially longitudinally, whose side wall comprises a plurality of successive indents in the shape of steps.

The pushing rod abuts at end of stroke, in other words in its final position, against an axial stop formed by the bottom of one of the successive indents of the side wall of the axial stop member.

Thus, the initial stop means, the intermediate stop means and the final stop means are particularly easy to make.

At least one from the initial axial stop member and the intermediate axial stop member comprises a pin arranged on its distal end, offset relative to the longitudinal axis of the pushing rod, cooperating with the actuation means to cause the rotation of at least one from the initial axial stop member and the intermediate axial stop member.

It is therefore particularly easy to manufacture such an axial stop member. We see that, since the pin is offset, it can be pushed in the transverse direction by the actuation means, thus generating the rotation about the longitudinal axis of the pushing rod of at least one from the initial axial stop member and the intermediate axial stop member, The implant injection device comprises a gripping unit and a support carrying the pushing rod slidably mounted relative to the gripping unit, preferably a sliding bush cooperating with a groove carried by the gripping unit, the support comprising a bearing surface intended to cooperate with the intermediate stop means to hold the pushing rod axially in the intermediate position.

Thus, the operation of such an implant injection device is simplified and more reliable. The use of a support for the pushing rod is particularly interesting in combination with the use of pushing means such as a spring, since this support can act as bearing surface for the spring, larger than the end of the pushing rod. In addition, the support slidably mounted in the gripping unit can guide and centre the pushing rod to prevent it from deviating under the thrust of the spring.

The pushing means comprise a thrust spring, resting between a gripping unit and the pushing rod, preferably arranged between the gripping unit and the support carrying the pushing rod.

The thrust spring can work in traction or in compression. Using a thrust spring to exert the thrust on the pushing rod is particularly interesting since the force of the thrust spring makes the injection easier and more precise, while being limited by at least the intermediate stop means, and possibly the initial and/or final stop means, so as not to inject an implant too slowly or too quickly, while allowing the user to control the start of injection of an implant. This is particularly advantageous to inject a plurality of implants. The maximum force exerted on the pushing rod is defined so as to avoid damaging the pushing rod and/or an implant.

The implant injection device comprises a removable locking element to lock the pushing means, configured to hold the implant injection device in a storage position, in particular in which the pushing rod is in its initial position.

Thus, the transport and handling of the implant injection device before its use are safer, since the implant injection device cannot be actuated accidentally or by being dropped.

The implant injection device comprises locking means arranged to block the pushing rod in its final position, position in which the pushing rod preferably projects towards the downstream direction past the end of the injection needle.

Thus, the implant injection device is not reusable, thereby respecting hygiene constraints relating to this type of implant injection device.

The implant injection device can inject a plurality of implants and comprises a plurality of respective intermediate stop means holding the pushing rod in a plurality of respective intermediate positions, said means opposing the force exerted by the pushing means when the stroke of the pushing rod reaches a respective predetermined distance corresponding to the length of injection of a respective implant.

Thus, the implant injection device can be adapted to the injection of any number n of implants, for example by including a number n−1 of intermediate stop means, which stop the displacement of the pushing rod after each implant injection, then release the displacement of the pushing rod from the respective intermediate position to a subsequent intermediate position or to the final position. Thus, such an implant injection device can be configured to inject more than two implants, for example between 3 and 50 implants, more precisely between 3 and 10 implants, even more precisely exactly 3, 4 or 5 implants.

The injection needle is attached to the gripping unit.

Thus, when the implant injection device is used by a user, the injection needle remains in a fixed position relative to the gripping unit. In particular, it does not retract either when injecting each implant of the plurality of implants or after injecting each implant of the plurality of implants. Consequently, this simplifies the design of the implant injection device.

The pushing means are automatic.

Thus, a user does not have to exert a pushing force in a distal direction on the pushing rod, which improves the actuation precision when the user actuates the actuation means. Consequently, this improves the precision of the injection process.

The pushing rod is configured to push the first implant and the second implant through the injection needle between a proximal initial position and a distal final position in which the first implant and the second implant are injected.

Thus, when the implant injection device is used by a user, the pushing rod is only displaced in the distal direction between the initial position and the final position. Consequently, this improves the precision of the injection process.

BRIEF DESCRIPTION OF THE DRAWINGS

It will be easier to understand the invention on reading the description below, given as an example and referring to the drawings, on which:

FIGS. 4 and 5 are side and perspective views of a part of the implant injection device of FIG. 1, in which the pushing rod is in an intermediate position;

FIG. 6 is a side and perspective view of a part of the implant injection device of FIG. 1, in which the pushing rod is in a final position;

FIG. 7 is a side and perspective view of a part of a gripping unit of the implant injection device of FIG. 1;

FIG. 8 is a side and perspective view of another part of a gripping unit of the implant injection device of FIG. 1.

DETAILED DESCRIPTION OF THE INVENTION

Figure 1:
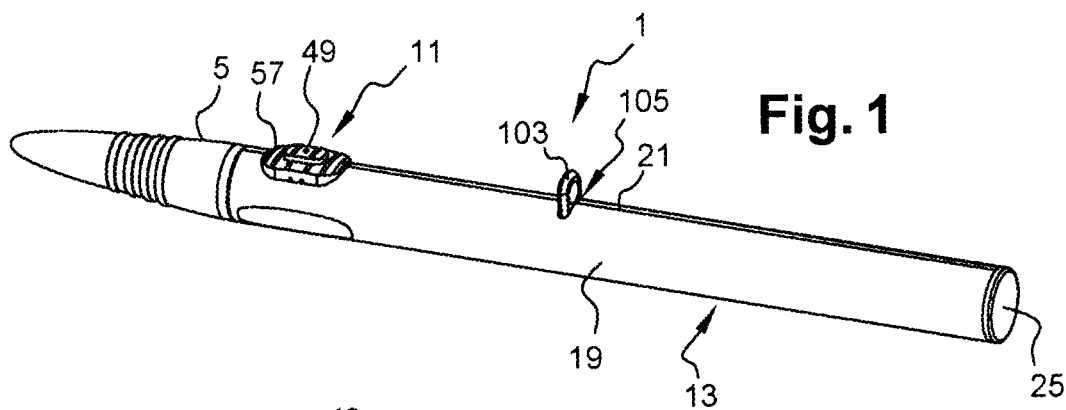
FIG. 1 is a perspective view of an implant injection device according to one embodiment, in storage configuration before injection.
Figure 2:
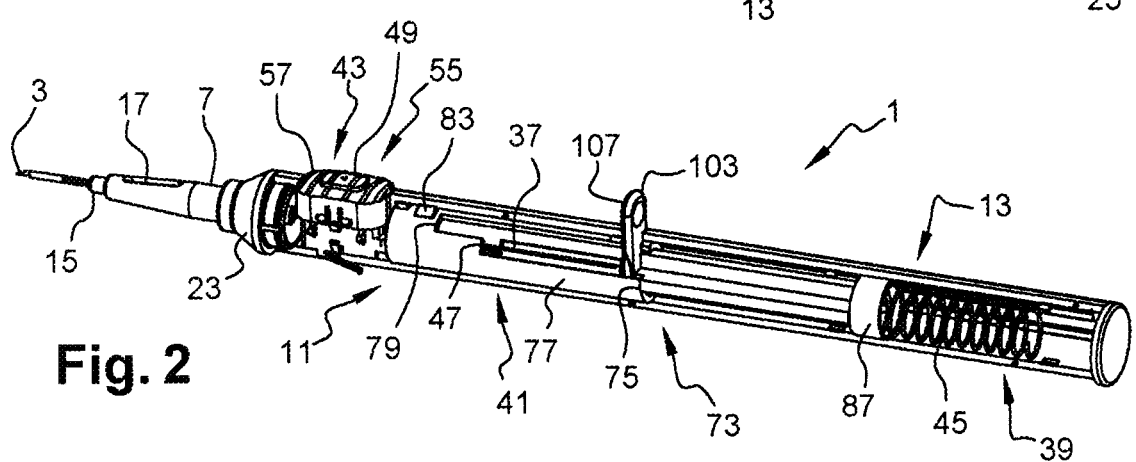
FIGS. 2 and 3 are side and perspective views of a part of the implant injection device of FIG. 1, in which the pushing rod is in an initial position.

As shown on FIGS. 1 and 2, an implant injection device 1 comprises an injection needle 3 protected by a cap 5, a receiver housing 7 for receiving at least a first implant and a second implant 9, injection means 11 and a gripping unit 13.

The implant injection device 1 is configured to inject several implants into a patient's body via the injection needle 3 shown on FIG. 2. In the example shown, the implant injection device 1 is configured to inject a first implant and a second implant 9 (shown on FIG. 5) into a patient's body via the injection needle 3. Although in the remainder of the document, the example is illustrated with two implants, the implant injection device 1 can also apply to a number of implants greater than two, such as for example three, four, five, ten implants.

As shown on FIGS. 2, 5 and 6, the injection needle 3 is hollow and is for example made of metal such as stainless steel. The injection needle 3 comprises a beveled distal end for easier insertion into the patient's body. The injection needle 3 carries a support element 15, which can be made of plastic and is intended to limit the depth of insertion of the injection needle 3 into the patient's body. The injection needle 3 is attached at its proximal end to the receiver housing 7. It can be protected in storage configuration by the cap 5.

The cap 5 is a cap protecting the injection needle 3, in this case it is assembled on the gripping unit 13, by clipping its proximal end to the gripping unit 13. However, other assembly means are possible, for example by screwing. In this example, the cap 5 is bullet-shaped, provided with reliefs for easier gripping.

The receiver housing 7 is a housing for receiving a first implant and a second implant 9. As shown on FIG. 2, the receiver housing 7 has a generally tubular and/or frustoconical shape, and houses the implants in its internal space, such that the implants are directed towards the injection needle 3, opposite the proximal end of the injection needle 3. In other words, the receiver housing 7 is arranged upstream from the injection needle 3, and is intended to receive the implants such that the implants are arranged upstream from the injection needle 3, in the injection direction of the injection needle 3. The receiver housing 7 is configured to contain two implants, the two implants being arranged one behind the other, in other words one upstream from the other, in the injection direction. In the example shown, the second implant 9 is arranged upstream from the first implant. The receiver housing 7 may comprise, at its distal end, an implant retaining means, such as a membrane or a slight narrowing of its inner diameter, intended to prevent an implant from falling through the injection needle 3, for example under the effect of the force of gravity. The receiver housing 7 may alternatively comprise, at its distal end, a flexible implant retaining element comprising an orifice of diameter less than that of the implants, the orifice being configured to deform and allow the implants to pass towards the injection needle 3 during the injection. The receiver housing 7 advantageously comprises a window 17, also called hole. Thus, a user can detect visually, through the window 17, the presence of the implants in the implant injection device 1, before performing the injection on a patient, when the cap 5 is removed. Note that in this example, the injection needle 3 and the receiver housing 7 are parts attached to each other, but that it would nevertheless be possible to consider that the injection needle 3 and the receiver housing 7 should form two portions of the same part, for example by being made in one piece. In addition, the receiver housing 7 is attached at its proximal end to the gripping unit 13, for example by clipping its proximal end to the gripping unit 13. Thus, the injection needle is attached to the gripping unit 13. The receiver housing 7 thus comprises a peripheral rib, which engages in a corresponding groove carried by the gripping unit 13. However, other assembly means are possible, for example by screwing. Alternatively, the receiver housing 7 could be formed directly in the gripping unit 13, being made in one piece with it. In this example, the receiver housing 7 is made of plastic, possibly partially or totally transparent.

In the example shown, the gripping unit 13 consists of several elements:
two half-shells 19, 21, shown in particular on FIG. 1,
a downstream plug 23, shown in particular on FIG. 2, and
an upstream plug 25, shown on FIG. 1.

In the assembled state, the two half-shells 19, 21, the downstream plug 23 and the upstream plug 25 are held in position relative to one another.

Each half-shell 19, 21 shown on FIGS. 7 and 8, comprises assembly means, for example brackets 27 and pins 29. Each half-shell 19, 21 further comprises housings 31 and receiving holes 33 intended to receive respectively, in the state assembled by clipping, the brackets 27 and pins 29 of the other half-shell 21, 19.

Figure 3:
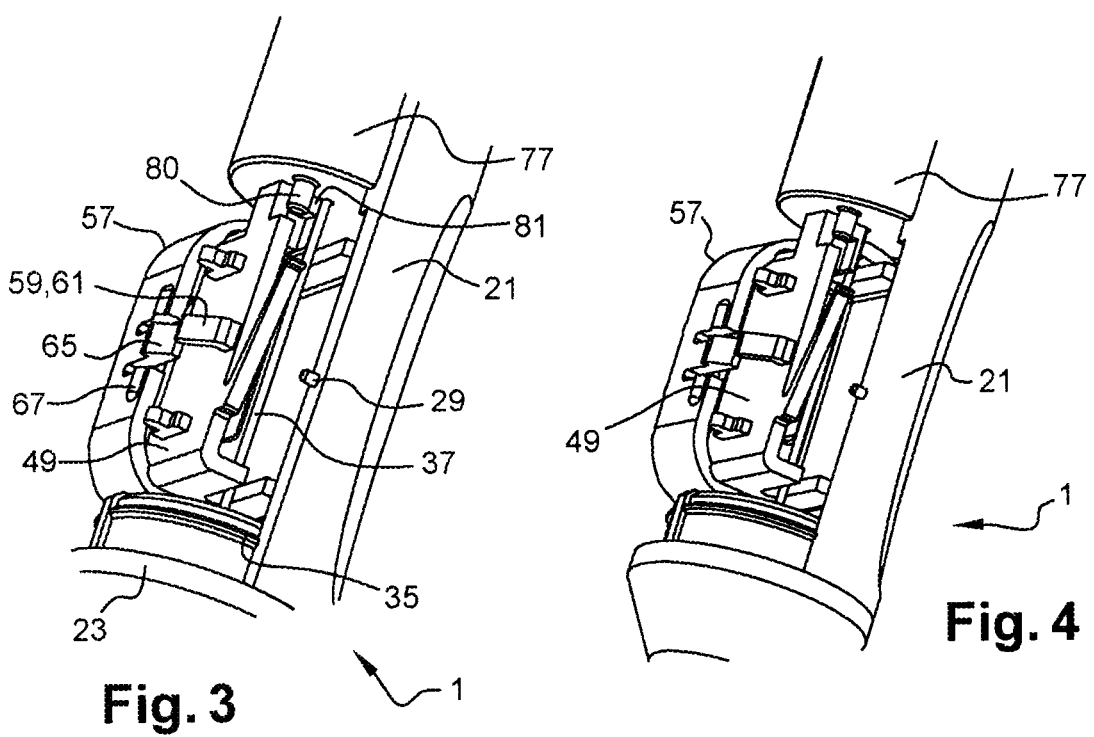

In addition, in the assembled state, the downstream plug 23 is in abutment against the distal end of the two half-shells 19, 21, and is assembled to the two half-shells 19, 21 by clipping a peripheral rib 35 as shown in particular on FIG. 3, in a corresponding inner peripheral groove 36 of each of the two half-shells 19, 21.

Similarly, the upstream plug 25 is in abutment against the proximal end of the two half-shells 19, 21, and is assembled to the two half-shells 19, 21 by clipping a peripheral rib in a corresponding inner peripheral groove of each of the two half-shells 19, 21.

Lastly, in the assembled state, the two half-shells 19, 21 house the injection means 11 and comprise an opening 38 through which at least part of the injection means 11 projects.

The injection means 11 comprise a pushing rod 37, pushing means 39, intermediate stop means 41 and actuation means 43 for actuation by a user.

The pushing rod 37 is arranged upstream from the implants 9 housed in the receiver housing 7. The pushing rod 37 extends longitudinally and is configured to push the first implant and the second implant 9 through the injection needle 3 between an initial position and a final position in which the first implant and the second implant 9 are injected. More precisely in this example, the pushing rod 37 is configured to push the first implant and the second implant 9 through the injection needle 3 between a proximal initial position and a distal final position in which the first implant and the second implant 9 are injected. Thus, in the initial position of the pushing rod 37, the first implant and the second implant 9 are housed in the receiver housing 7, and in the final position of the pushing rod 37, the first implant and the second implant 9 have passed through the injection needle 3 and are a priori placed in a patient's body. The pushing rod 37 can be made of metal, for example steel, preferably stainless steel.

In this example, the pushing means 39 are automatic and, in this example, comprise a thrust spring 45 resting between the gripping unit 13 and the pushing rod 37. The pushing means 39, due to the action of the thrust spring 45, are thus configured to exert a force tending to move the pushing rod 37 from the initial position to the final position. In particular, as shown on FIG. 2, the thrust spring 45 is a spring working in compression. Alternatively, the thrust spring can be a spring working in traction.

The intermediate stop means 41 hold the pushing rod 37 in an intermediate position between the initial position and the final position. The intermediate stop means 41 oppose the force exerted by the pushing means 39 when the stroke of the pushing rod 37 reaches a predetermined distance corresponding to the length of injection of the first implant.

The intermediate stop means 41 comprise an intermediate axial stop member 47 holding the pushing rod 37 in the intermediate position, the intermediate axial stop member 47 being configured to be driven by the actuation means 43 to release a displacement of the pushing rod 37 from the intermediate position to the final position.

The actuation means 43 for actuation by a user, configured to actuate a displacement of the pushing rod 37 from the initial position to the final position, comprise an actuation button 49 which can be moved by pressing by a user between:
a rest position before actuation, a median position, in which the actuation means 43 release the displacement of the pushing rod 37 from its initial position to its intermediate position, and a terminal position, in which the actuation means 43 release the displacement of the pushing rod 37 from its intermediate position to its final position.

The actuation button 49 is placed in the opening 38 formed in the two half-shells 19, 21 so that it can be actuated by a user. Thus, the actuation means 43, in particular the actuation button 49, are lateral, movable by sliding in a radial direction relative to the longitudinal axis of the pushing rod 37. Alternatively, the actuation means 43 can be movable by pivoting about an axis orthogonal to the longitudinal axis of the pushing rod 37, or by pivoting about the longitudinal axis of the pushing rod 37, and comprise for example a pivoting bush.

The actuation means 43 comprise means 51 for returning the actuation button 49 to its rest position, shown on FIG. 6, in particular an elastic tab 53 carried by the actuation button 49. In this example in particular, the actuation button 49 comprises two elastic tabs 53 extending from a surface of the actuation button, opposite a surface on which a user presses, and opposite an inner wall of the half-shells 19, 21. One of two elastic lugs 53 extends in the downstream direction from an upstream part of this surface, and the other extends in the upstream direction from a downstream part of this surface. Alternatively, the return means 51 is a spring.

Figure 4:
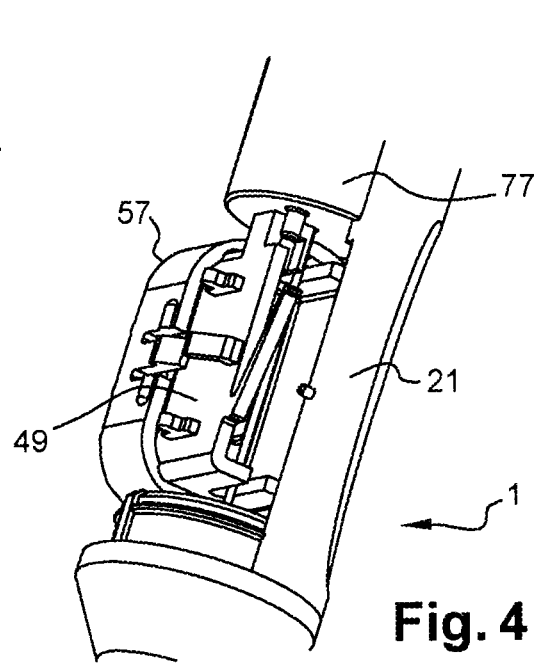

The actuation means 43 further comprise an indication element 55, shown on FIG. 2, configured to indicate to a user that the actuation button 49 is in its median position. Thus, the indication element 55 comprises a secondary button 57 (shown on FIG. 4) flush with the actuation button 49 when the latter is in its median position.

The secondary button 57 is arranged around the actuation button 49. It is slidably mounted relative to the gripping unit 13 and to the actuation button 49. The secondary button 57 is movable between two positions, one in which the secondary button 57 is flush with the actuation button 49 when the latter is in its median position, and the other in which the secondary button 57 is flush with the actuation button 49 when the latter is in its terminal position. "Flush" should preferably be understood to mean that the surface on which a user presses on the secondary button 57 is level with the surface on which a user presses on the actuation button 49. In addition, in its rest position, the actuation button 49 projects relative to the secondary button 57.

The implant injection device 1 also comprises non-return means 59 (shown on FIG. 3) preventing the actuation button 49 from returning respectively from its median position and from its terminal position. The non-return means 59 are in particular formed by clipping means. To prevent the return from its terminal position, the clipping means are formed by brackets 61 (shown on FIG. 3) located each side of the actuation button 49, said clipping means clipping into housings 63 (shown on FIGS. 7 and 8) located on the gripping unit 13, in particular on an inner wall of each half-shell 19, 21. To prevent the return from its median position, the clipping means are for example formed by gadroons located on the upstream and downstream ends of the actuation button 49, said gadroons clipping into corresponding grooves formed on the secondary button 57. The secondary button 57 is itself held in position relative to the gripping unit 13 by clipping means such as brackets 65 (shown on FIG. 3) and/or gadroons 67 (shown on FIG. 3), said clipping means clipping respectively into housings 69 and/or grooves 71 (shown on FIG. 7) formed on the gripping unit 13, in particular on the half-shells 19, 21.

The implant injection device 1 further comprises initial stop means 73 (shown on FIG. 1) opposing the force exerted by the pushing means 39 and holding the pushing rod 37 in the initial position.

The initial stop means 73 comprise an initial axial stop member 75 holding the pushing rod 37 in the initial position, the initial axial stop member 75 being configured to be driven by the actuation means 43 to release a displacement of the pushing rod 37 from the initial position to the intermediate position. In particular, the initial axial stop member 75 and the intermediate axial stop member 47 are made in one piece and form an axial stop member 77, as shown in particular on FIG. 2, and are for example made of the same material.

The axial stop member 77 is formed by a partly hollowed out cylinder which is directed substantially longitudinally, whose side wall comprises a plurality of successive indents 75, 47, 79 in the shape of steps. The pushing rod 37 abuts at end of stroke, in other words in its final position, against a final axial stop member 79 formed by the bottom of one of the successive indents 75, 47, 79 of the side wall of the axial stop member 77.

The actuation means 43 cause the rotation of at least one from the initial axial stop member 75 and the intermediate axial stop member 47, in particular of the axial stop member 77, to release respectively a displacement of the pushing rod 37 from the initial position to the intermediate position and/or from the intermediate position to the final position.

To do this, at least one from the initial axial stop member 75 and the intermediate axial stop member 47, in particular the axial stop member 77, comprises a pin 80 (shown on FIG. 3) arranged on their distal end, offset relative to the longitudinal axis of the pushing rod 37, cooperating with the actuation means 43 to cause the rotation of at least one from the initial axial stop member 75 and the intermediate axial stop member 47. In particular, the pin 80 cooperates with a substantially flat surface 81 (shown on FIG. 3) of the actuation button 49.

The axial stop member 77 comprises a stop protrusion 83 (shown on FIG. 2), which cooperates with a groove 85 formed around the periphery of the half-shell 19 as shown on FIG. 8, so as to abut against the other half-shell 21 when the pushing rod 37 is in its initial position, as shown on FIG. 2. This prevents accidental rotation of the axial stop member 77, which could affect the release of the displacement of the pushing rod 37 from the initial position to the intermediate position.

The implant injection device 1 also comprises a support 87 carrying the pushing rod 37. The support 87 is slidably mounted relative to the gripping unit 13. In particular, the support 87 is a sliding bush cooperating with a groove carried by the gripping unit 13.

In the example shown in particular on FIG. 5, the support 87 cooperates with a groove 89 (shown on FIG. 8) carried by the half-shell 19 and with a groove 91 carried by the other half-shell 21. The support 87 thus comprises a generally cross-shaped cross-section, and has four ribs. Two opposite ribs 93 each cooperate with one of the grooves 89, 91, and two other ribs 95 cooperate by sliding in the inner wall of the axial stop member 77 to allow relative sliding between the support 87 and the axial stop member 77.

The downstream end of each rib 93 forms a bearing surface 97 cooperating with the intermediate stop means 41 to hold the pushing rod 37 axially in the intermediate position, as shown on FIG. 5. In particular, the bearing surface 97 cooperates with the initial axial stop member 75 when the pushing rod 37 is in the initial position, with the intermediate stop member 47 when the pushing rod 37 is in the intermediate position, and with the final axial stop member 79 when the pushing rod 37 is in the final position.

The support 87 comprises, at its upstream end, a bush 99 for receiving the thrust spring 45, and at its downstream end, a bush 101 for supporting the pushing rod 37. Thus, the thrust spring 45 is arranged between the gripping unit 13 and the support 87 carrying the pushing rod 37.

The implant injection device 1, as shown on FIG. 1, further comprises a removable locking element 103 to lock the pushing means 39, configured to hold the implant injection device 1 in a storage position, in which the pushing rod 37 is in its initial position.

Thus, to hold the implant injection device 1 in its storage position, the removable locking element 103 is engaged through an opening 105 formed in the gripping unit 13, in particular in a complementary manner on each half-shell 19, 21, and formed in the axial stop member 77. As shown on FIG. 2, one end of the removable locking element 103 consists of a gripping end 107. The other end, for example, consists of two branches, in particular C-shaped, which are configured to engage in a peripheral groove formed on the support 87 of the pushing rod 37. Thus, the support 87 is prevented from moving in the injection direction, the forces being transmitted from the pushing means 39 formed by the thrust spring 45 to the support 87, then from the support 87 to the removable locking element 103, and from the removable locking element 103 to the gripping unit 13 at the walls of the opening 105. Thus, the removable locking element 103 must be removed before using the implant injection device 1 to inject the implants into a patient's body.

The implant injection device 1 comprises locking means arranged to block the pushing rod 37 in its final position, position in which the pushing rod 37 preferably projects towards the downstream direction past the end of the injection needle 3, as shown on FIG. 6. Thus, in this final position, a lug supported by the axial stop member 77 cooperates with a recess carried by the gripping unit 13, preventing the pushing rod 37 from returning in a direction opposite to the injection direction. This is a simple way of preventing the implant injection device 1 from being reused and also prevents injury due to the injection needle 3, for example if the implant injection device 1 is dropped after use, since the pushing rod 37 projects past the end of the injection needle 3 and is blocked by these locking means.

The elements of the implant injection device 1, whose material is not specified in this description, may be made of a thermoplastic material, for example polyethylene or polypropylene.

An example of operation of the implant injection device 1 will now be described.

The implant injection device 1 as shown on FIG. 1 is in storage configuration before use.

The user must remove the cap 5 protecting the injection needle 3, as shown on FIG. 2—the implant injection device 1 being considered to be assembled—and check that the implants are present by looking through the window 17 of the receiver housing 7. The user must then remove the removable locking element 103 to avoid blocking the displacement of the pushing rod 37 from its initial position to its final position. In this configuration in initial position, the rib 93 of the support 87 of the pushing rod 37 is in abutment against the initial axial stop member 75, and the actuation button 49 is in rest position.

The injection needle 3 is then inserted into the patient's body and the user presses the actuation button 49. The actuation button 49 then slides radially relative to the gripping unit 13 and moves from its rest position to its median position. The pin 80 of the axial stop member 77 is then driven by the displacement of the surface 81 of the actuation button 49. By means of the pin 80, the axial stop member 77 is then driven in rotation, which releases the displacement of the support 87 and of the pushing rod 37, the pushing rod 37 then moving from its initial position to its intermediate position. In this configuration in intermediate position, the rib 93 of the support 87 of the pushing rod 37 abuts against the intermediate axial stop member 47, which may generate a tactile or audible indication such as a vibration and/or an audible "click", due to the impact of the rib 93 against the intermediate axial stop member 47. The actuation button 49 is then in its median position in which the secondary button 57 is flush with the actuation button 49. In this intermediate configuration, a first implant has been injected into the patient's body. Optionally, this step may be followed by a step of changing the injection location or of modifying the direction of the injection needle 3, for example so that the second implant 9 is injected at the same depth as the first implant.

The user then presses the actuation button 49 and the secondary button 57, the two buttons being flush. The actuation button 49 and the secondary button 57 then slide radially relative to the gripping unit 13, and the actuation button 49 moves from its median position to its terminal position. The pin 80 of the axial stop member 77 is then driven by the displacement of the surface 81 of the actuation button 49. By means of the pin 80, the axial stop member 77 is then driven in rotation, which releases the displacement of the support 87 and of the pushing rod 37, the pushing rod 37 then moving from its intermediate position to its final position. In this configuration in intermediate position, the rib 93 of the support 87 of the pushing rod 37 abuts against the final axial stop member 79, which may generate a tactile or audible indication such as a vibration and/or an audible "click", due to the impact of the rib 93 against the final axial stop member 79. The actuation button 49 is then in its terminal position in which the secondary button 57 is still flush with the actuation button 49. In this terminal configuration, a last implant, in this case the second implant 9, has been injected into the patient's body, and the pushing rod 37 projects towards the downstream direction past the end of the injection needle 3. Lastly, the user removes the implant injection device 1 from the patient's body.

The invention is not limited to the embodiments described and other embodiments will be clearly apparent to those skilled in the art. Although the invention has been illustrated with an implant injection device 1, configured to inject two implants, those skilled in the art will easily understand that such an implant injection device 1 can be configured to inject a number of implants greater than two, for example three, four, five or even ten implants. In this case, the number of intermediate stop means, in particular intermediate axial stop members, is chosen according to the number of implants to be injected and is equal to this number minus one. Thus, the invention also relates to an implant injection device of the above-mentioned type, which can inject a plurality of implants and comprising a plurality of respective intermediate stop means holding the pushing rod in a plurality of respective intermediate positions, said means opposing the force exerted by the pushing means when the stroke of the pushing rod reaches a respective predetermined distance corresponding to the length of injection of a respective implant.

The invention claimed is:

1. An implant injection device, comprising:
   an injection needle,
   a receiver housing for receiving at least a first implant and a second implant,
   an injection mechanism, comprising:
   a pushing rod, arranged upstream from said first implant and said second implant housed in the receiver housing and configured to push the first implant and the second implant through the injection needle, wherein the pushing rod is configured to move between an initial position and a final position in which the first implant and the second implant are injected,
   a pushing device for pushing on the pushing rod, configured to exert a force to move the pushing rod from the initial position to the final position, wherein the pushing device is automatic,
   an intermediate stop device holding the pushing rod in an intermediate position between the initial position and the final position, said intermediate stop device being configured to oppose the force exerted by the pushing device to move the pushing rod from the initial position to the final position when a stroke of the pushing rod reaches a predetermined distance corresponding to a length of injection of the first implant, and
   an actuator for actuation by a user, configured to release the pushing rod from the intermediate position to the final position.

2. The implant injection device according to claim 1, further comprising an initial stop device opposing the force exerted by the pushing device to move the pushing rod from the initial position to the final position and holding the pushing rod in the initial position.

3. The implant injection device according to claim 2, wherein the initial stop device comprises an initial axial stop member holding the pushing rod in the initial position, the initial axial stop member being configured to be driven by the actuator to release the pushing rod from the initial position to the intermediate position.

4. The implant injection device according to claim 3, wherein the actuator is configured to cause rotation of at least one of the initial axial stop member and the intermediate axial stop member to release respectively the pushing rod from the initial position to the intermediate position and/or from the intermediate position to the final position.

5. The implant injection device according to claim 4, wherein at least one of the initial axial stop member and the intermediate axial stop member comprises a pin arranged on a distal end of the initial axial stop member or a distal end of the intermediate axial stop member, offset relative to a longitudinal axis of the pushing rod, cooperating with the actuator to cause the rotation of at least one of the initial axial stop member and the intermediate axial stop member.

6. The implant injection device according to claim 1, wherein the actuator comprises an actuation button which can be moved by pressing by the user between:
   a rest position before actuation,
   a median position, in which the actuator releases the pushing rod from the initial position to the intermediate position, and
   a terminal position, in which the actuator releases the pushing rod from the intermediate position to the final position.

7. The implant injection device according to claim 6, wherein the actuator comprises an indication element configured to indicate to the user that the actuation button is in the median position, the indication element comprising a secondary button flush with the actuation button when the actuation button is in the median position.

8. The implant injection device according to claim 6, wherein the actuator comprises an elastic tab carried by the actuation button, or a spring, for returning the actuation button to the rest position.

9. The implant injection device according to claim 6, comprising a non-return device preventing the actuation button from returning respectively from the median position and from the terminal position.

10. The implant injection device according to claim 1, wherein the actuator is lateral and movable by sliding in a radial direction relative to a longitudinal axis of the pushing rod or by pivoting about an axis orthogonal to the longitudinal axis of the pushing rod.

11. The implant injection device according to claim 1, wherein the intermediate stop device comprises an intermediate axial stop member holding the pushing rod in the intermediate position, the intermediate axial stop member being configured to be driven by the actuator to release the pushing rod from the intermediate position to the final position.

12. The implant injection device according to claim 1, comprising a gripping unit and a support carrying the pushing rod slidably mounted relative to the gripping unit, wherein the support is a sliding bush cooperating with a groove carried by the gripping unit, the support comprising a bearing surface intended to cooperate with the intermediate stop device to hold the pushing rod axially in the intermediate position.

13. The implant injection device according to claim 1, wherein the pushing device comprises a thrust spring resting between a gripping unit and the pushing rod arranged between the gripping unit and a support carrying the pushing rod.

14. The implant injection device according to claim 1, further comprising a removable locking element to lock the pushing device, configured to hold the implant injection device in a storage position, in which the pushing rod is in its initial position.

15. The implant injection device according to claim 1, further comprising a locking member arranged to block the pushing rod in the final position in which the pushing rod projects towards a downstream direction past an end of the injection needle.

16. The implant injection device according to claim 1, which can inject a plurality of implants and comprising a plurality of respective intermediate stop devices holding the pushing rod in a plurality of respective intermediate positions, said plurality of respective intermediate stop devices opposing the force exerted by the pushing device to move the pushing rod from the initial position to the final position when the stroke of the pushing rod reaches a respective predetermined distance corresponding to a length of injection of a respective implant.

* * * * *